(12) United States Patent
Opolski et al.

(10) Patent No.: US 8,870,913 B2
(45) Date of Patent: Oct. 28, 2014

(54) CATCH SYSTEM WITH LOCKING CAP FOR PATENT FORAMEN OVALE (PFO) OCCLUDER

(75) Inventors: Steven W. Opolski, Carlisle, MA (US); Stephanie M. Kladakis, Watertown, MA (US); Ryan Cahill, Brighton, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 1517 days.

(21) Appl. No.: 11/728,906

(22) Filed: Mar. 27, 2007

(65) Prior Publication Data

US 2007/0250115 A1    Oct. 25, 2007

Related U.S. Application Data

(60) Provisional application No. 60/787,990, filed on Mar. 31, 2006.

(51) Int. Cl.
 *A61B 17/08* (2006.01)
 *A61B 17/00* (2006.01)
 *A61B 17/12* (2006.01)

(52) U.S. Cl.
 CPC ... *A61B 17/0057* (2013.01); *A61B 2017/00575* (2013.01); *A61B 2017/00606* (2013.01); *A61B 2017/00592* (2013.01); *A61B 2017/00619* (2013.01); *A61B 2017/00623* (2013.01); *A61B 17/12022* (2013.01)
 USPC .......................................... 606/213; 606/151

(58) Field of Classification Search
 USPC .......... 606/213, 215, 151, 157, 158, 214, 216
 See application file for complete search history.

(56) References Cited

U.S. PATENT DOCUMENTS

| 3,824,631 A | 7/1974 | Burstein et al. |
| 3,874,388 A | 4/1975 | King et al. |

(Continued)

FOREIGN PATENT DOCUMENTS

| DE | 9413645 U1 | 10/1994 |
| EP | 0362113 | 4/1990 |

(Continued)

OTHER PUBLICATIONS

Athanasion, T., "Coronary Artery Bypass with the Use of a Magnetic Distal Anastomotic Device: Surgical Technique and Preliminary Experience," The Heart Surgery Forum #2004-1024, 2004, 4 pgs.

(Continued)

*Primary Examiner* — Dianne Dornbusch
*Assistant Examiner* — Alexander Orkin
(74) *Attorney, Agent, or Firm* — DLA Piper LLP (US)

(57) ABSTRACT

Devices, delivery systems and delivery techniques for an occlusion device for the closure of physical anomalies, such as an atrial septal defect, a patent foramen ovale (PFO), and other septal and vascular defects are described. The devices, delivery systems and delivery techniques relate particularly to, but are not limited to, a patent foramen ovale (PFO) occluder made from a polymer tube. In certain embodiments, the occluder includes a catch system that holds the occluder in the deployed, expanded profile. The catch system includes a locking funnel cap. In some embodiments, the locking funnel cap forces the proximal ends of the occluder in a radially inward position to lock the catch member in place and prevent the occluder from moving from its deployed configuration.

17 Claims, 5 Drawing Sheets

(56) References Cited

U.S. PATENT DOCUMENTS

| | | |
|---|---|---|
| 3,875,648 A | 4/1975 | Bone |
| 3,924,631 A | 12/1975 | Mancusi |
| 4,006,747 A | 2/1977 | Kronenthal et al. |
| 4,007,743 A | 2/1977 | Blake |
| 4,149,327 A | 4/1979 | Hammer et al. |
| 4,425,908 A | 1/1984 | Simon |
| 4,610,674 A | 9/1986 | Suzuki et al. |
| 4,626,245 A | 12/1986 | Weinstein |
| 4,696,300 A | 9/1987 | Anderson |
| 4,710,192 A | 12/1987 | Liotta et al. |
| 4,836,204 A | 6/1989 | Landymore et al. |
| 4,840,623 A | 6/1989 | Quackenbush |
| 4,902,508 A | 2/1990 | Badylak et al. |
| 4,915,107 A | 4/1990 | Rebuffat et al. |
| 4,917,089 A | 4/1990 | Sideris |
| 4,956,178 A | 9/1990 | Badylak et al. |
| 5,021,059 A | 6/1991 | Kensey et al. |
| 5,037,433 A | 8/1991 | Wilk et al. |
| 5,041,129 A | 8/1991 | Hayhurst et al. |
| 5,078,736 A | 1/1992 | Behl |
| 5,106,913 A | 4/1992 | Yamaguchi et al. |
| 5,108,420 A | 4/1992 | Marks |
| 5,149,327 A | 9/1992 | Oshiyama et al. |
| 5,167,363 A | 12/1992 | Adkinson et al. |
| 5,167,637 A | 12/1992 | Okada et al. |
| 5,171,259 A | 12/1992 | Inoue et al. |
| 5,192,301 A | 3/1993 | Kamiya et al. |
| 5,222,974 A | 6/1993 | Kensey et al. |
| 5,226,879 A | 7/1993 | Ensminger et al. |
| 5,236,440 A | 8/1993 | Hlavacek |
| 5,245,023 A | 9/1993 | Peoples et al. |
| 5,245,080 A | 9/1993 | Aubard et al. |
| 5,250,430 A | 10/1993 | Peoples et al. |
| 5,257,637 A | 11/1993 | El Gazayerli |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,316,262 A | 5/1994 | Koebler |
| 5,334,217 A | 8/1994 | Das |
| 5,350,363 A | 9/1994 | Goode et al. |
| 5,354,308 A | 10/1994 | Simon et al. |
| 5,411,481 A | 5/1995 | Allen et al. |
| 5,413,584 A | 5/1995 | Schulze et al. |
| 5,417,699 A | 5/1995 | Klein et al. |
| 5,425,744 A | 6/1995 | Fagan et al. |
| 5,433,727 A | 7/1995 | Sideris |
| 5,451,235 A | 9/1995 | Lock et al. |
| 5,478,353 A | 12/1995 | Yoon |
| 5,480,353 A | 1/1996 | Garza, Jr. |
| 5,480,424 A | 1/1996 | Cox |
| 5,486,193 A | 1/1996 | Bourne et al. |
| 5,507,811 A | 4/1996 | Koike et al. |
| 5,534,432 A | 7/1996 | Peoples et al. |
| 5,540,712 A | 7/1996 | Kleshinski et al. |
| 5,562,632 A | 10/1996 | Davila et al. |
| 5,577,299 A | 11/1996 | Thompson et al. |
| 5,601,571 A | 2/1997 | Moss |
| 5,618,311 A | 4/1997 | Gryskiewicz |
| 5,620,461 A | 4/1997 | Muijs Van De Moer et al. |
| 5,626,599 A | 5/1997 | Bourne et al. |
| 5,634,936 A | 6/1997 | Linden et al. |
| 5,649,950 A | 7/1997 | Bourne et al. |
| 5,649,959 A | 7/1997 | Hannam et al. |
| 5,663,063 A | 9/1997 | Peoples et al. |
| 5,683,411 A | 11/1997 | Kavteladze et al. |
| 5,690,674 A | 11/1997 | Diaz |
| 5,693,085 A | 12/1997 | Buirge et al. |
| 5,702,421 A | 12/1997 | Schneidt et al. |
| 5,709,707 A | 1/1998 | Lock et al. |
| 5,717,259 A | 2/1998 | Schexnayder |
| 5,720,754 A | 2/1998 | Middleman et al. |
| 5,725,552 A | 3/1998 | Kotula et al. |
| 5,733,294 A | 3/1998 | Forber et al. |
| 5,733,337 A | 3/1998 | Carr, Jr. et al. |
| 5,741,297 A | 4/1998 | Simon |
| 5,776,162 A | 7/1998 | Kleshinski |
| 5,776,183 A | 7/1998 | Kanesaka et al. |
| 5,797,960 A | 8/1998 | Stevens et al. |
| 5,800,516 A | 9/1998 | Fine et al. |
| 5,810,884 A | 9/1998 | Kim |
| 5,823,956 A | 10/1998 | Roth et al. |
| 5,829,447 A | 11/1998 | Stevens et al. |
| 5,853,420 A | 12/1998 | Chevillon et al. |
| 5,853,422 A | 12/1998 | Huebsch et al. |
| 5,855,614 A | 1/1999 | Stevens et al. |
| 5,861,003 A | 1/1999 | Latson et al. |
| 5,865,791 A | 2/1999 | Whayne et al. |
| 5,879,366 A | 3/1999 | Shaw et al. |
| 5,893,856 A | 4/1999 | Jacob et al. |
| 5,902,319 A | 5/1999 | Daley |
| 5,904,703 A | 5/1999 | Gilson |
| 5,919,200 A | 7/1999 | Stambaugh et al. |
| 5,924,424 A | 7/1999 | Stevens et al. |
| 5,928,250 A | 7/1999 | Koike et al. |
| 5,944,738 A | 8/1999 | Amplatz et al. |
| 5,955,110 A | 9/1999 | Patel et al. |
| 5,976,174 A | 11/1999 | Ruiz |
| 5,989,268 A | 11/1999 | Pugsley, Jr. et al. |
| 5,993,475 A | 11/1999 | Lin et al. |
| 5,993,844 A | 11/1999 | Abraham et al. |
| 5,997,575 A | 12/1999 | Whitson et al. |
| 6,010,517 A | 1/2000 | Baccaro |
| 6,024,756 A | 2/2000 | Huebsch et al. |
| 6,030,007 A | 2/2000 | Bassily et al. |
| 6,056,760 A | 5/2000 | Koike et al. |
| 6,071,998 A | 6/2000 | Muller et al. |
| 6,077,291 A | 6/2000 | Das |
| 6,077,880 A | 6/2000 | Castillo et al. |
| 6,079,414 A | 6/2000 | Roth |
| 6,080,182 A | 6/2000 | Shaw et al. |
| 6,096,347 A | 8/2000 | Geddes et al. |
| 6,106,913 A | 8/2000 | Scardino et al. |
| 6,113,609 A | 9/2000 | Adams |
| 6,117,159 A | 9/2000 | Huebsch et al. |
| 6,126,686 A | 10/2000 | Badylak et al. |
| 6,132,438 A | 10/2000 | Fleischman et al. |
| 6,143,037 A | 11/2000 | Goldstein et al. |
| 6,152,144 A | 11/2000 | Lesh et al. |
| 6,165,183 A | 12/2000 | Kuehn et al. |
| 6,165,204 A | 12/2000 | Levinson et al. |
| 6,171,329 B1 | 1/2001 | Shaw et al. |
| 6,174,322 B1 | 1/2001 | Schneidt et al. |
| 6,174,330 B1 | 1/2001 | Stinson |
| 6,187,039 B1 | 2/2001 | Hiles et al. |
| 6,190,353 B1 | 2/2001 | Makower et al. |
| 6,206,895 B1 | 3/2001 | Levinson |
| 6,206,907 B1 | 3/2001 | Marino et al. |
| 6,214,029 B1 | 4/2001 | Thill et al. |
| 6,217,590 B1 | 4/2001 | Levinson |
| 6,221,092 B1 | 4/2001 | Koike et al. |
| 6,227,139 B1 | 5/2001 | Nguyen et al. |
| 6,228,097 B1 | 5/2001 | Levinson et al. |
| 6,231,561 B1 | 5/2001 | Frazier et al. |
| 6,245,080 B1 | 6/2001 | Levinson |
| 6,245,537 B1 | 6/2001 | Williams et al. |
| 6,261,309 B1 | 7/2001 | Urbanski |
| 6,265,333 B1 | 7/2001 | Dzenis et al. |
| 6,270,515 B1 | 8/2001 | Linden et al. |
| 6,277,138 B1 | 8/2001 | Levinson et al. |
| 6,277,139 B1 | 8/2001 | Levinson et al. |
| 6,287,317 B1 | 9/2001 | Makower et al. |
| 6,290,674 B1 | 9/2001 | Roue et al. |
| 6,299,635 B1 | 10/2001 | Frantzen |
| 6,306,150 B1 | 10/2001 | Levinson |
| 6,306,424 B1 | 10/2001 | Vyakarnam et al. |
| 6,312,446 B1 | 11/2001 | Huebsch et al. |
| 6,315,791 B1 | 11/2001 | Gingras et al. |
| 6,316,262 B1 | 11/2001 | Huisman et al. |
| 6,319,263 B1 | 11/2001 | Levinson |
| 6,322,548 B1 | 11/2001 | Payne et al. |
| 6,328,727 B1 | 12/2001 | Frazier et al. |

(56) References Cited

U.S. PATENT DOCUMENTS

| | | |
|---|---|---|
| 6,334,872 B1 | 1/2002 | Termin et al. |
| 6,342,064 B1 | 1/2002 | Koike et al. |
| 6,344,048 B1 | 2/2002 | Chin et al. |
| 6,344,049 B1 | 2/2002 | Levinson et al. |
| 6,346,074 B1 | 2/2002 | Roth |
| 6,348,041 B1 | 2/2002 | Klint et al. |
| 6,352,552 B1 | 3/2002 | Levinson et al. |
| 6,355,052 B1 | 3/2002 | Neuss et al. |
| 6,356,782 B1 | 3/2002 | Sirimanne et al. |
| 6,364,853 B1 | 4/2002 | French et al. |
| 6,371,904 B1 | 4/2002 | Sirimanne et al. |
| 6,375,625 B1 | 4/2002 | French et al. |
| 6,375,671 B1 | 4/2002 | Kobayashi et al. |
| 6,379,342 B1 | 4/2002 | Levinson |
| 6,379,368 B1 | 4/2002 | Corcoran et al. |
| 6,387,104 B1 | 5/2002 | Pugsley, Jr. et al. |
| 6,398,796 B2 | 6/2002 | Levinson |
| 6,402,772 B1 | 6/2002 | Amplatz et al. |
| 6,419,669 B1 | 7/2002 | Frazier et al. |
| 6,426,145 B1 | 7/2002 | Moroni |
| 6,436,088 B2 | 8/2002 | Frazier et al. |
| 6,440,152 B1 | 8/2002 | Gainor et al. |
| 6,460,749 B1 | 10/2002 | Levinson et al. |
| 6,482,224 B1 | 11/2002 | Michler et al. |
| 6,488,706 B1 | 12/2002 | Solymar et al. |
| 6,494,888 B1 | 12/2002 | Laufer et al. |
| 6,508,828 B1 | 1/2003 | Akerfeldt et al. |
| 6,514,515 B1 | 2/2003 | Williams |
| 6,548,569 B1 | 4/2003 | Williams et al. |
| 6,551,303 B1 | 4/2003 | Van Tassel et al. |
| 6,551,344 B2 | 4/2003 | Thill |
| 6,585,755 B2 | 7/2003 | Jackson et al. |
| 6,596,013 B2 | 7/2003 | Yang et al. |
| 6,599,448 B1 | 7/2003 | Ehrhard, Jr. et al. |
| 6,610,764 B1 | 8/2003 | Martin et al. |
| 6,623,508 B2 | 9/2003 | Shaw et al. |
| 6,623,518 B2 | 9/2003 | Thompson et al. |
| 6,626,936 B2 | 9/2003 | Stinson |
| 6,629,901 B2 | 10/2003 | Huang |
| 6,666,861 B1 | 12/2003 | Grabek |
| 6,669,722 B2 | 12/2003 | Chen et al. |
| 6,689,589 B2 | 2/2004 | Huisman et al. |
| 6,712,804 B2 | 3/2004 | Roue et al. |
| 6,712,836 B1 | 3/2004 | Berg et al. |
| 6,726,696 B1 | 4/2004 | Houser et al. |
| 6,828,357 B1 | 12/2004 | Martin et al. |
| 6,838,493 B2 | 1/2005 | Williams et al. |
| 6,867,247 B2 | 3/2005 | Williams et al. |
| 6,867,248 B1 | 3/2005 | Martin et al. |
| 6,867,249 B2 | 3/2005 | Lee et al. |
| 6,921,410 B2 | 7/2005 | Porter |
| 2001/0010481 A1 | 8/2001 | Blanc et al. |
| 2001/0014800 A1 | 8/2001 | Frazier et al. |
| 2001/0025132 A1 | 9/2001 | Alferness et al. |
| 2001/0034537 A1 | 10/2001 | Shaw et al. |
| 2001/0034567 A1 | 10/2001 | Allen et al. |
| 2001/0037129 A1 | 11/2001 | Thill |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0022860 A1 | 2/2002 | Borillo et al. |
| 2002/0026208 A1 | 2/2002 | Roe et al. |
| 2002/0029048 A1 | 3/2002 | Miller |
| 2002/0032459 A1 | 3/2002 | Horzewski et al. |
| 2002/0032462 A1 | 3/2002 | Houser et al. |
| 2002/0034259 A1 | 3/2002 | Tada |
| 2002/0035374 A1 | 3/2002 | Borillo et al. |
| 2002/0043307 A1 | 4/2002 | Ishida et al. |
| 2002/0049457 A1 | 4/2002 | Kaplan et al. |
| 2002/0052572 A1 | 5/2002 | Franco et al. |
| 2002/0058989 A1 | 5/2002 | Chen et al. |
| 2002/0077555 A1 | 6/2002 | Schwartz |
| 2002/0095174 A1 | 7/2002 | Tsugita et al. |
| 2002/0096183 A1 | 7/2002 | Stevens et al. |
| 2002/0099389 A1 | 7/2002 | Michler et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111537 A1 | 8/2002 | Taylor et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0164729 A1 | 11/2002 | Skraly et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor et al. |
| 2003/0004533 A1 | 1/2003 | Dieck et al. |
| 2003/0023266 A1 | 1/2003 | Welch et al. |
| 2003/0028213 A1 | 2/2003 | Thill et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0057156 A1 | 3/2003 | Peterson et al. |
| 2003/0059640 A1 | 3/2003 | Marton et al. |
| 2003/0065379 A1 | 4/2003 | Babbs et al. |
| 2003/0100920 A1 | 5/2003 | Akin et al. |
| 2003/0113868 A1 | 6/2003 | Flor et al. |
| 2003/0120337 A1 | 6/2003 | Van Tassel et al. |
| 2003/0139819 A1 | 7/2003 | Beer et al. |
| 2003/0171774 A1 | 9/2003 | Freudenthal et al. |
| 2003/0191495 A1 | 10/2003 | Ryan et al. |
| 2003/0195530 A1 | 10/2003 | Thill |
| 2003/0204203 A1 | 10/2003 | Khairkhahan et al. |
| 2004/0044361 A1 | 3/2004 | Frazier et al. |
| 2004/0073242 A1 | 4/2004 | Chanduszko |
| 2004/0176799 A1 | 9/2004 | Chanduszko et al. |
| 2004/0210301 A1 | 10/2004 | Obermiller |
| 2004/0234567 A1 | 11/2004 | Dawson |
| 2005/0025809 A1 | 2/2005 | Hasirci et al. |
| 2005/0043759 A1 | 2/2005 | Chanduszko |
| 2005/0125032 A1* | 6/2005 | Whisenant et al. ........... 606/213 |
| 2005/0267523 A1 | 12/2005 | Devellian et al. |
| 2005/0273135 A1 | 12/2005 | Chanduszko et al. |
| 2005/0288786 A1 | 12/2005 | Chanduszko |
| 2006/0122647 A1 | 6/2006 | Callaghan et al. |
| 2006/0198869 A1* | 9/2006 | Furst et al. ................. 424/426 |
| 2006/0265004 A1 | 11/2006 | Callaghan et al. |
| 2007/0010851 A1 | 1/2007 | Chanduszko et al. |
| 2007/0162071 A1* | 7/2007 | Burkett et al. ............... 606/200 |
| 2007/0167981 A1 | 7/2007 | Opolski |

FOREIGN PATENT DOCUMENTS

| | | |
|---|---|---|
| EP | 0474887 A1 | 3/1992 |
| EP | 0 839 549 | 5/1998 |
| EP | 1013227 A2 | 6/2000 |
| EP | 1046375 A1 | 10/2000 |
| EP | 1222897 A2 | 7/2002 |
| WO | WO-96/25179 | 8/1996 |
| WO | WO-96/31157 | 10/1996 |
| WO | WO-98/07375 | 2/1998 |
| WO | WO-98/08462 | 3/1998 |
| WO | WO-98/16174 | 4/1998 |
| WO | WO-98/29026 | 7/1998 |
| WO | WO-98/51812 | 11/1998 |
| WO | WO-99/05977 | 2/1999 |
| WO | WO-98/18864 | 4/1999 |
| WO | WO-99/18862 | 4/1999 |
| WO | WO-99/18864 | 4/1999 |
| WO | WO-99/18870 | 4/1999 |
| WO | WO-99/18871 | 4/1999 |
| WO | WO-00/27292 | 5/2000 |
| WO | WO-00/44428 | 8/2000 |
| WO | WO-01/21247 | 3/2001 |
| WO | WO-01/30268 | 5/2001 |

(56) References Cited

FOREIGN PATENT DOCUMENTS

| | | |
|---|---|---|
| WO | WO-01/49185 | 7/2001 |
| WO | WO-01/78596 | 10/2001 |
| WO | WO-02/17809 | 3/2002 |
| WO | WO-02/24106 | 3/2002 |
| WO | WO-03/024337 | 3/2003 |
| WO | WO-03/053493 | 7/2003 |
| WO | WO-03/059152 | 7/2003 |
| WO | WO-03/077733 | 9/2003 |
| WO | WO-03/082076 | 10/2003 |
| WO | WO-03/103476 | 12/2003 |
| WO | WO-2004/043266 | 5/2004 |
| WO | WO-2004/043508 | 5/2004 |
| WO | WO-2004/052213 | 6/2004 |
| WO | WO-2005/006990 | 1/2005 |
| WO | WO-2005/018728 | 3/2005 |
| WO | WO-2005/027752 | 3/2005 |
| WO | WO-2005/074813 | 8/2005 |
| WO | WO-2005/092203 | 10/2005 |
| WO | WO-2005/110240 | 11/2005 |
| WO | WO-2005/112779 | 12/2005 |
| WO | WO-2006/036837 | 4/2006 |
| WO | WO-2006/102213 | 9/2006 |

OTHER PUBLICATIONS

Bachthaler, M. et al., "Corrosion of Tungsten Coils After Peripheral Vascular Embolization Theraphy: Influence on Outcome and Tungsten Load", *Catherization and Cardiovascular Interventions*, vol. 62, pp. 380-384, 2004.

European Examination Report, European Application No. 04781644.2, mailed Aug. 23, 2007 (3 Pages).

Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.

Filsoufi, F., et al., "Automated Distal Coronary Bypass with a Novel Magnetic Coupler (MVP system)," J. Thoracic and Cardiovascular Surgery, vol. 127(1), pp. 185-192.

International Search Report for International Patent Application No. PCT/EP06/010783, mailed May 4, 2007 (6 pgs).

International Search Report, International Application No. PCT/US02/40850 mailed Jun. 19, 2003 (4 pgs).

International Search Report, International Application No. PCT/US03/01050, mailed Jul. 8, 2003 (1 pg).

International Search Report, International Application No. PCT/US03/09051, mailed Sep. 29, 2003 (2 pgs).

International Search Report, International Application No. PCT/US03/17390, mailed Oct. 6, 2003 (4 pgs).

International Search Report, International Application No. PCT/US03/17715, mailed Mar. 24, 2004 (2 pgs).

International Search Report, International Application No. PCT/US03/32133, mailed Apr. 22, 2004 (1 pg).

International Search Report for International Patent Application No. PCT/US03/34003, mailed Mar. 10, 2004 (4 pgs).

International Search Report, International Application No. PCT/US03/35479, mailed Apr. 14, 2004 (2 pages).

International Search Report, International Application No. PCT/US03/35998 mailed Jun. 16, 2004 (5 pgs).

International Search Report, International Application No. PCT/US03/39253, mailed Apr. 19, 2004 (4 pgs).

International Search Report, International Application No. PCT/US04/022643, mailed Mar. 31, 2005 (2 pgs).

International Search Report, International Application No. PCT/US04/026998, mailed Apr. 22, 2005 (5 pgs).

International Search Report, International Application No. PCT/US04/029978, mailed Jan. 26, 2005 (3 pgs).

International Search Report, International Application No. PCT/US05/006703, mailed Jul. 25, 2005 (3 pgs).

International Search Report, International Application No. PCT/US05/013705 mailed Aug. 4, 2005 (4 pgs).

International Search Report, International Application No. PCT/US05/015382, mailed Oct. 6, 2005 (4 pgs).

International Search Report, International Application No. PCT/US06/09978, mailed Jul. 13, 2006 (2 pgs).

International Search Report, International Application No. PCT/US07/065546, mailed Oct. 29, 2007. 4 pages.

International Search Report, International Application No. PCT/US2007/065526, mailed Aug. 8, 2007 (5 pgs).

International Search Report for International Patent Application No. PCT/US07/065532, mailed Sep. 14, 2007 (5 pgs).

International Search Report, International Application No. PCT/US2007/065541, mailed Aug. 7, 2007 (4 pgs).

International Search Report, International Application No. PCT/US97/14822, mailed Feb. 20, 1998 (2 pgs).

International Search Report, International Application No. PCT/US97/17927, mailed Feb. 10, 1998 (1 pg).

Isotalo, T. et al., "Biocompatibility Testing of a New Bioabsorbable X-Ray Positive SR-PLA 96/4 Urethral Stent", *The Journal of Urology*, vol. 163, pp. 1764-1767, Nov. 1999.

Kimura, A.., et al., "Effects of Neutron Irradiation on the Transformation Behavior in Ti—Ni Alloys," Abstract, Proceedings of the Int'l Conf. on Mariensitic Transformations, 1992, pp. 935-940.

Klima, U., "Magnetic Vascular Port in Minimally Invasive Direct Coronary Artery Bypass Grafting," Circulation, 2004, II-55-II-60.

Meier, MD, Bernhard, et al., "Contemporary Management of Patent Foramen Ovale," American Heart Association, Inc., Circulation, 2003, vol. 107, pp. 5-9.

Parviainen, M. et al., "A New Biodegradable Stent for the Pancreaticojejunal Anastomosis After Pancreaticoduodenal Resection: In Vitro Examination and Pilot Experiences in Humans", *Pancreas*, vol. 21, No. 1, pp. 14-21, 2000.

Ramanathan, G., et al., "Experimental and Computational Methods for Shape Memory Alloys," 15th ASCE Engineering Mechanics Conference, Jun. 2-5, 2002.

Ruddy, A.C. et al., "Rheological, Mechanical and Thermal Behaviour of Radipaque Filled Polymers", *Polymer Processing Research Centre, School of Chemical Engineering, Queen's University of Belfast*, 5 pages.

Ruiz, et al., "The Puncture Technique: A New Method for Transcatheter Closure of Patent Foramen Ovale," Catheterization and Cardiovascular Interventions, 2001, vol. 53, pp. 369-372.

Shabalovskaya, S., "Surface, Corrosion amd Biocompatibility Aspects of Nitinol as and Implant Material," Bio-Medical Materials and Engineering, 2002, vol. 12, pp. 69-109.

SMST-2000, "Proceedings of the International Conference on Shape Memory and Superelastic Technologies," Apr. 30 to May 4, 2000, Asilomar Conference Center.

Stockel, "Nitinol Medical Devices and Implants," SMST-2000 Conference Proceedings, 2001, pp. 531-541.

Uchil, J., "Shape Memory Alloys—Characterization Techniques," Pramana—Journal of Physics, 2002, vol. 58(5)(6), pp. 1131-1139.

Vaajanen, A. et al., "Expansion and Fixation Properties of a New Braided Biodegradable Urethral Stent: An Experimental Study in the Rabbit", *The Journal of Urology*, vol. 169, pp. 1771-1174, Mar. 2003.

* cited by examiner

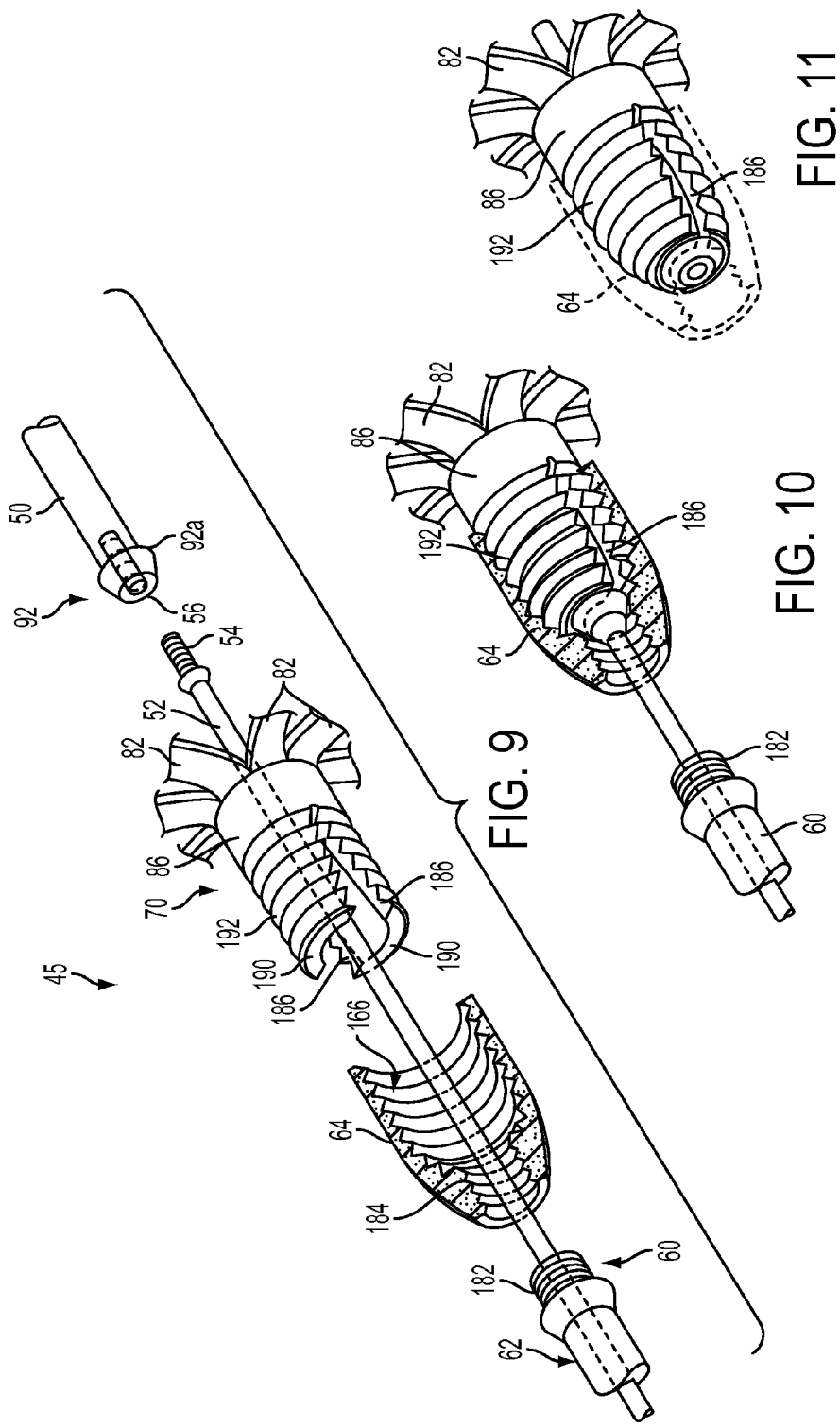

CATCH SYSTEM WITH LOCKING CAP FOR PATENT FORAMEN OVALE (PFO) OCCLUDER

CROSS-REFERENCE TO RELATED APPLICATIONS

This application claims the benefit under 35 U.S.C. 119(e) of U.S. Provisional Application No. 60/787,990, filed on Mar. 31, 2006, which is incorporated by reference herein in its entirety.

FIELD OF THE INVENTION

This invention relates generally to occlusion devices for the closure of physical anomalies, such as an atrial septal defect, a patent foramen ovale, and other septal and vascular defects. In particular, this invention relates to a catch mechanism to maintain the occluder in the deployed configuration. The invention also relates to delivery systems and mechanisms for such devices.

BACKGROUND OF THE INVENTION

A patent foramen ovale (PFO), illustrated in FIG. 1, is a persistent, one-way, usually flap-like opening in the wall between the right atrium 11 and left atrium 13 of the heart 10. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 11 to the left atrium 13 and blood clots could enter the systemic circulation. It is desirable that this circumstance be eliminated.

The foramen ovale serves a desired purpose when a fetus is gestating. Because blood is oxygenated through the umbilical cord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two overlapping layers of tissue: septum primum 14 and septum secundum 16. However, a PFO has been shown to persist in a number of adults.

The presence of a PFO is generally considered to have no therapeutic consequence in otherwise healthy adults. Paradoxical embolism via a PFO is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO and the risk for paradoxical embolism or stroke. In addition, there is significant evidence that patients with a PFO who have had a cerebral vascular event are at increased risk for future, recurrent cerebrovascular events. Another condition, chronic migraine headache, has also been linked to the presence of a PFO. Although this relationship is also not well understood, and research investigating this link is currently ongoing, PFO closure has been shown to eliminate or significantly reduce migraine headaches in many patients.

In certain cases, such as when anticoagulation is contraindicated, surgery may be necessary or desirable to close a PFO. The surgery would typically include suturing a PFO closed by attaching septum secundum to septum primum. This sutured attachment can be accomplished using either an interrupted or a continuous stitch and is a common way a surgeon shuts a PFO under direct visualization.

Umbrella devices and a variety of other similar mechanical closure devices, developed initially for percutaneous closure of atrial septal defects (ASDs), have been used in some instances to close PFOs. These devices potentially allow patients to avoid the side effects often associated with anticoagulation therapies and the risks of invasive surgery. However, umbrella devices and the like that are designed for ASDs are not optimally suited for use as PFO closure devices.

Currently available septal closure devices present drawbacks, including technically complex implantation procedures. Additionally, there are significant complications due to thrombus, fractures of the components, conduction system disturbances, perforations of heart tissue, arrhythmia and residual leaks. Many devices have high septal profile and include large masses of foreign material, which may lead to unfavorable body adaptation of a device. Given that ASD devices are designed to occlude holes, many lack anatomic conformability to the flap-like anatomy of PFOs. Thus, when inserting an ASD device to close a PFO, the narrow opening and the thin flap may form impediments to proper deployment. Even if an occlusive seal is formed, the device may be deployed in the heart on an angle, leaving some components insecurely seated against the septum and, thereby, risking thrombus formation due to hemodynamic disturbances. Finally, some septal closure devices are complex to manufacture, which may result in inconsistent product performance.

Various devices and delivery systems have been developed to deliver occluders and other medical devices through body lumens. Some delivery systems of the prior art are used to deliver devices that readily expand to a delivered configuration when removed from the delivery system. Other occluders do not readily expand into a deployed configuration and techniques are used to cause the device to change into the deployed configuration. In the latter case, once an occluder is delivered to the desired delivery site and deployed, the occluder must have a catch system that keeps the device in the deployed configuration.

The devices and techniques disclosed herein are designed to address these and other deficiencies of prior art septal closure devices and techniques for delivering and retrieving such devices.

BRIEF SUMMARY OF THE INVENTION

Aspects of the present invention relate to devices and techniques for delivering a device into a desired location within the body and for securing the device in the deployed configuration. This device relates particularly to, but is not limited to, septal occluders made from a polymer tube. The device further relates to, but is not limited to, septal occluders made from filaments. These delivery techniques, in addition to use with septal occluders, could be applied to other medical devices, such as other expandable devices constructed from an underlying tubular structure.

In one aspect, the occluder includes a first side adapted to be disposed on one side of the septal tissue and a second side adapted to be disposed on the opposite side of the septal tissue. The first and second sides are adapted to occlude the aperture upon deployment of the device at its intended deployment location. The device also includes a catch system that maintains the configuration of the device once it has been deployed. In one aspect, the invention includes a delivery system for delivering an occluder that closes an aperture in septal tissue. In certain embodiments, a delivery system includes a delivery catheter in which the occluder and the catch system are provided and a delivery wire for holding and deploying the catch system.

In one aspect, the catch system includes a locking funnel cap with a threaded inner surface that is threadably attached to the proximal end of an occluder. In one aspect, the locking funnel cap cooperates with a catch member that extends inside an axial passage provided within the occluder body. In some embodiments, the passage is radially central. In some embodiments, the catch member has a distal flange that engages the distal end of the occluder and a proximal flange that engages the proximal end of the occluder in the deployed configuration. In some embodiments, the locking funnel cap secures the proximal end of the catch member to the proximal end of the occluder in the deployed configuration, and more specifically, prevents the proximal end of the catch member from being drawn back into the occluder passage. The device is configured such that upon threadably connecting the locking funnel cap with the proximal end of the occluder, the locking funnel cap applies a radial force on the proximal end of the occluder to secure the catch member proximal to the occluder and thereby catch the occluder in its deployed configuration. The delivery system is then detached from the locking funnel cap and the deployment process is completed. The locking funnel cap remains with the occluder inside the patient's body at the delivered location.

According to at least some embodiments, the occluder is formed from a tube. According to some embodiments, the tube includes a material selected from the group consisting of metals, shape memory materials, alloys, polymers, bioabsorbable polymers, and combinations thereof. In particular embodiments, the tube includes a shape memory polymer. In particular embodiments, the tube includes nitinol. In some embodiments, the tube is formed by rolling a flat piece of material into a tubular form. According to some embodiments, the occluder is formed by cutting the tube. In other embodiments, the occluder is formed from a plurality of filaments, aligned in a tubular arrangement and bonded at selected locations. The occluder is placed in its deployment configuration by reducing the axial length of the device.

These and other aspects and embodiments of the present invention are illustrated and described below.

BRIEF DESCRIPTION OF THE DRAWINGS

Aspects of the present invention may be more fully understood from the following description and accompanying drawings, in which:

FIG. 9 is an exploded view of a catch system in accordance with an embodiment of the present invention;

FIGS. 10 and 11 are assembled views of a catch system and a portion of the occluder according to an embodiment of the present invention.

DETAILED DESCRIPTION OF THE INVENTION

Figure 1:
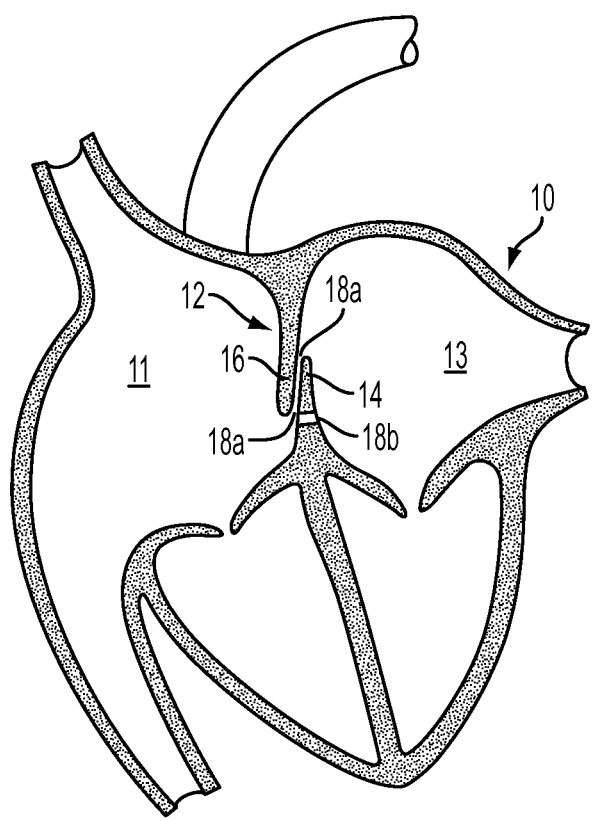
FIG. 1 is a schematic representation of a human heart including various septal defects.

Aspects of the present invention include devices, delivery/retrieval systems and techniques for delivering such devices intended to occlude an aperture within body tissue. In particular and as described in detail below, the described devices may be used for closing an ASD, ventricular septal defect (VSD), or PFO in the heart. Although the embodiments are described with reference to an ASD, VSD or PFO, one skilled in the art will recognize that the device and methods of the present invention may be used to treat other anatomical conditions. As such, the invention should not be considered limited in applicability to any particular anatomical condition. In addition, the systems and methods for delivery and retrieval, and for catching the device in its deployed configuration, which are aspects of the present invention may also be used in connection with other types of devices, in particular, devices having tubular profiles.

In this application, "distal" refers to the direction away from a catheter insertion location and "proximal" refers to the direction nearer the insertion location. Additionally, the term "delivery configuration" refers to the configuration of a device, such as an occluder, when it has an axially elongated profile in a delivery catheter. The term "deployed configuration" refers to the configuration of the device, such as an occluder, when it has a radially expanded profile, such as at the desired implantation location. The reference numerals used to identify components of the disclosed embodiments are located where the component is illustrated. At times a reference numeral may be applied to a component not described in connection with the Figure. The identification of the component is to facilitate an overall understanding of the disclosed embodiment.

In this description, terms "internal threads," "threaded inner surface," and "female threads" are used interchangeably, i.e., intended to be synonyms. Terms "external threads," "threaded outer surface," and "male threads" are also used interchangeably, i.e., intended to be synonyms.

FIG. 1 illustrates a human heart 10, having a right atrium 11 and a left atrium 13 and including various anatomical apertures 18a and 18b. The atrial septum 12 includes septum primum 14 and septum secundum 16. The anatomy of the septum 12 varies widely within the population. In some people, septum primum 14 extends to and overlaps with septum secundum 16. The septum primum 14 may be quite thin. When the anatomical apertures 18a is present, blood could travel through the anatomical aperture 18a between septum primum 14 and septum secundum 16 (referred to as "the PFO tunnel"). Additionally or alternatively, blood could also travel through the anatomical aperture 18b between septum primum 14 and septum secundum 16 (referred to as ASD).

Figure 2:
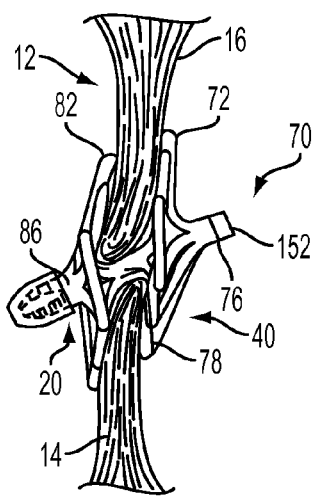
FIG. 2 illustrates a deployed occluder according to an aspect of the present invention.

FIG. 2 illustrates an exemplary occluder with which systems and techniques disclosed herein may be used. An occluder 70, for example, is illustrated as deployed in the septum 12 of a heart, with the locking system engaged. The occluder 70 operates to close an aperture in the septum 12 by covering both sides of the aperture.

Figure 3:
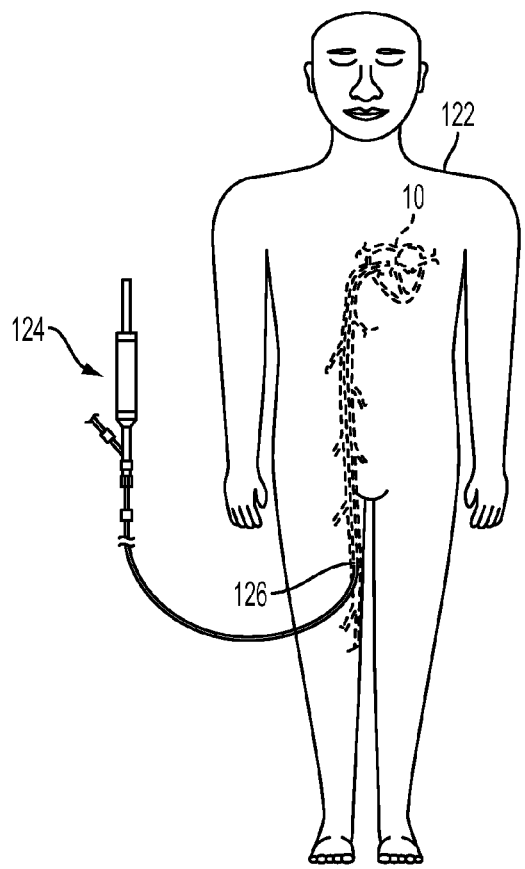
FIG. 3 illustrates introduction of an occluder in a human heart using a delivery system in accordance with an aspect of the present invention.
Figure 4:
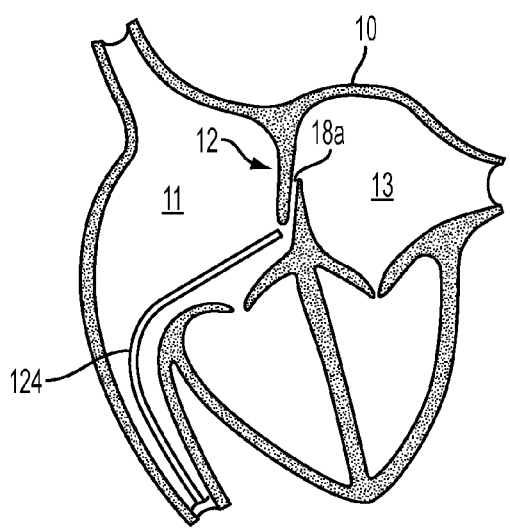
FIG. 4 illustrates a detail view of a delivery catheter in a heart with its tip approaching a PFO between the left atrium and right atrium.

FIG. 3 illustrates the insertion of an occluder in a human subject 122 using a delivery assembly 124 in accordance with an aspect of the disclosure. A portion of delivery assembly 124, including an occluder and a delivery mechanism for the occluder, which can be externally manipulated by a clinician, is inserted into the subject through an incision point 126. The distal end of the delivery assembly is advanced toward and into the heart 10 until the distal end is in proximity to the defect to be closed, as seen in FIG. 4.

The embodiment described in conjunction with FIGS. 5-8 has some similarities to the device disclosed in or can be used in conjunction with catch mechanisms and delivery/retrieval systems and techniques disclosed in U.S. patent application Ser. No. 10/890,784, entitled Tubular Patent Foramen Ovale (PFO) Closure Device with Catch System filed on Jul. 14, 2004; U.S. patent application Ser. No. 11/395,718, entitled Tubular Patent Foramen Ovale (PFO) Closure Device with Catch System, filed Mar. 31, 2006; U.S. patent application Ser. No. 11/384,635, filed Mar. 20, 2006, entitled Catch Member for PFO Occluder; U.S. patent application Ser. No. 11/235,661, filed Sep. 26, 2005, entitled Occluder Device Double Securement System for Delivery/Recovery of Such Occluder Device; U.S. patent application Ser. No. 11/121, 833, entitled Catching Mechanisms for Tubular Septal Occluder, filed May 4, 2005; U.S. patent application Ser. No. 60/787,988, entitled Deformable Flap Catch Mechanism for Occluder Device, filed Mar. 31, 2006; and U.S. patent application Ser. No. 11/644,373, entitled Catch Members for Occluder Devices, filed Dec. 21, 2006; and U.S. patent application Ser. No. TBD, entitled Patent Foramen Ovale (PFO) closure Device with Linearly Elongating Petals, filed Mar. 27, 2007, all of which have the same assignee as the present application, and are incorporated herein by reference in their entirety. These incorporated documents describe some ways in which a device can be formed and how to deliver such a device.

Figure 5:
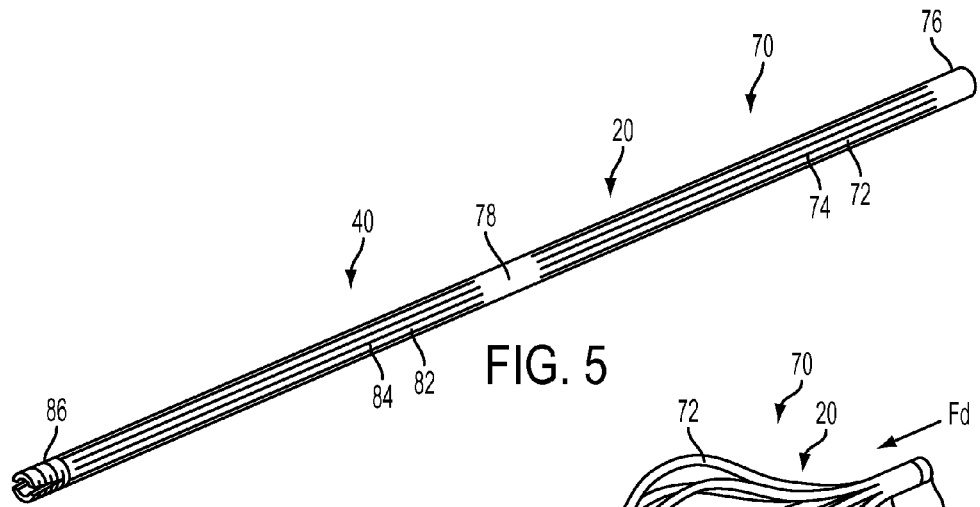
FIGS. 5-8 illustrate an occluder according to an aspect of the present invention in a sequence between a delivery configuration (FIG. 5) and a deployed profile deployed configuration (FIG. 8)
Figure 6:
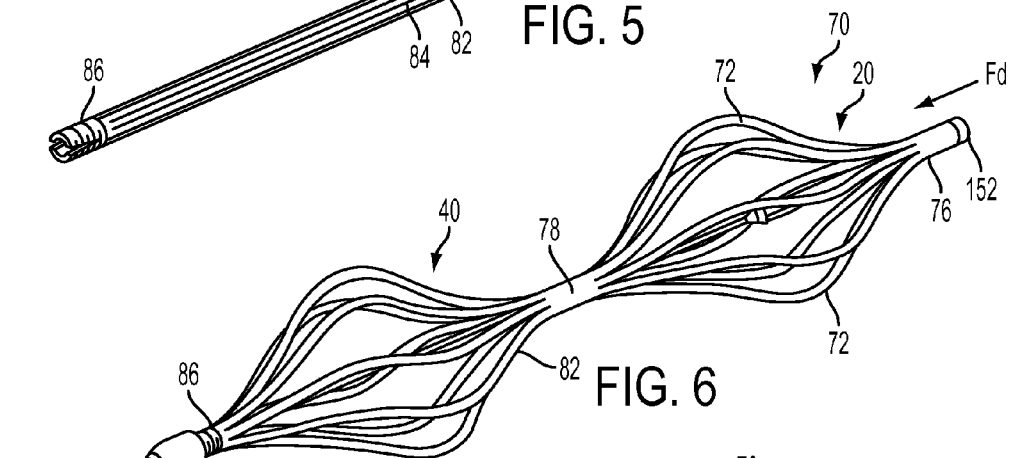
Figure 7:
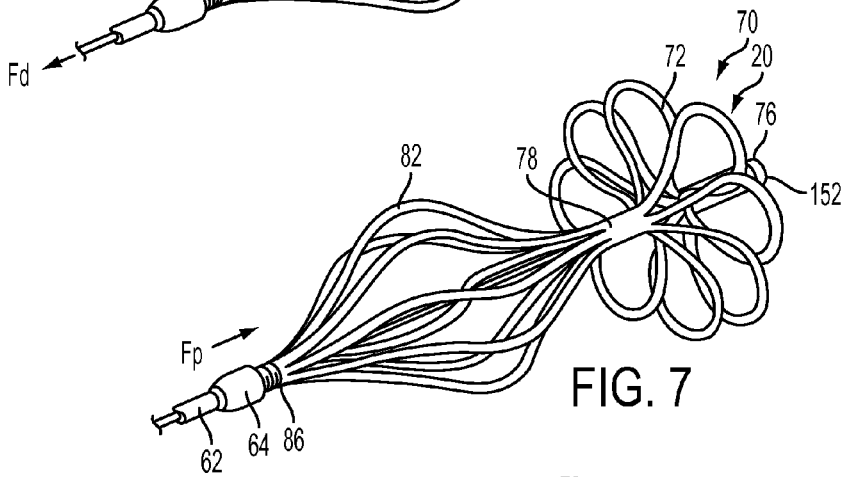
Figure 8:
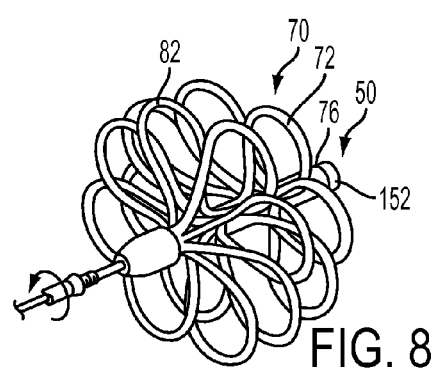

As shown in FIGS. 5-8, the occluder 70 is formed from a tube (which can be extruded or rolled). The occluder 70 has a distal portion 20 and a proximal portion 40. Distal petals 72 are produced in the occluder 70 by slits 74 in the upper portion of tube according to the cutting pattern shown in FIG. 5. The segments are illustrated in FIG. 6. The distal portion 20 of the tube includes eight slits 74 that define eight extended segments of the tube that form the distal loops or petals 72. As is apparent from the figures, the slits 74 extend the entire distance of the distal portion of the tube between central tube 78 and distal end 76 so that loops of the same cross-section are formed. Upon application of force $F_d$ to distal end 76, the segments defined by slits 74 bow and twist outward to form distal petals 72. The movement of the segments during deployment is such that the segments rotate in an orthogonal plane relative to the axis of the device. Central tube 78 may be constrained during the application of force $F_d$, or any combination of forces sufficient to reduce the axial length of the tube may be applied. One end of each of distal petals 72 originates from central tube 78, while the other end originates from distal end 76 (FIGS. 6 and 7). Proximal petals 82, as shown in FIGS. 6-8, are produced by slits 84 between central tube 78 and proximal end 86, using the same cutting pattern described above. Similarly upon application of force $F_p$ to proximal end 86 or a combination of forces sufficient to reduce the axial length of the tube, segments defined by slits 84 bow and twist outward to form proximal petals 82 in proximal portion 40 of the occluder 70. One end of each of distal petals 82 originates from central tube 78, while the other end originates from proximal end 86.

The tube(s), or filaments in certain embodiments, forming occluder 70 may be formed from a biocompatible metal or polymer. In at least some embodiments, the occluder 70 is formed of a bioabsorbable polymer, or a shape memory polymer. Shape memory polymers can be advantageous so that the structure of the device assists in pressing the PFO tunnel closed. In other embodiments, the occluder 70 is formed of a biocompatible metal, such as a shape memory alloy (e.g., nitinol). The thermal shape memory and/or superelastic properties of shape memory polymers and alloys permit the occluder 70 to resume and maintain its intended shape in vivo despite being distorted during the delivery process. Alternatively, or additionally, the occluder 70 may be formed of a bioabsorbable metal, such as iron, magnesium, or combinations of these and similar materials. Exemplary bioabsorbable polymers include polyhydroxyalkanoate compositions, for example poly-4-hydroxybutyrate (P4HB) compositions, disclosed in U.S. Pat. No. 6,610,764, entitled Polyhydroxyalkanoate Compositions Having Controlled Degradation Rate and U.S. Pat. No. 6,548,569, entitled Medical Devices and Applications of polyhydroxyalkanoate Polymers, both of which are incorporated herein by reference in their entirety.

The cross-sectional shape of the tube may be circular or polygonal, for example square, or hexagonal. The slits 74, 84 may be disposed on the face of the polygon (i.e., the flat part) or on the intersection of the faces.

The tube can be injection molded, extruded, or constructed of a sheet of material and rolled into a tube. The sheet of material could be a single ply sheet or multiple ply. The slits that form the segments can be cut or stamped into the sheet prior to rolling the sheet into a tube to connect the ends to form an enclosed cross section. Various geometrical cross sections are possible including circular, square, hexagonal and octagonal, and the joint could be at the vertex or along the flat of a wall if the cross section is of a particular geometry. Various attachment techniques can be used to join the ends of the sheet to form a tube, including welding, heat adhesives, non-heat adhesives and other joining techniques suitable for in-vivo application.

Occluder 70 may be made in any one of several ways. Slits 74 and 84 may be cut such that the tube bends into its intended configuration following deployment in vivo. Specifically, slits 74 and 84 may be cut to produce segments 72 and 82 (as illustrated in FIGS. 5, 6) of a thickness that facilitates the bending and formation of loops 72 and 82 (as illustrated in FIGS. 7, 8) upon the application of forces $F_d$ and/or $F_p$ during deployment. Alternatively and/or additionally, after cutting the slits, a tube formed of a shape memory material may be preformed into its intended configuration ex vivo so that it will recover its preformed shape once deployed in vivo. According to at least some embodiments, this preforming technique produces more reliable deployment of occluder 70 in vivo. An intermediate approach may also be used: the tube may be only slightly preformed ex vivo such that it is predisposed to bend into its intended deployed shape in vivo upon application of forces $F_d$ and $F_p$. Similarly, a filament-based occluder can also be preformed or partially preformed prior to delivery and deployment.

The petal configuration, illustrated in FIG. 8, is the deployed configuration of the occluder 70. The transformable design of occluder 70 enables occluder 70 to be delivered in a low profile, delivery configuration and to be converted readily, i.e., by reducing the axial length, in place to the relatively high profile deployed configuration. Moreover, the conversion can readily be effected by forcing distal end 76 and proximal end 86 together. For example, distal portion 20 and proximal portion 40 of occluder 70 may be deployed in separate steps, or both distal portion 20 and proximal portion 40 of occluder 70 may be exposed (e.g., out of the delivery catheter) prior to engaging the catch system and deployed together as the catch system is engaged. Use of the terms distal and proximal portion 20 and 40, respectively, include the loops or other geometries and configurations that are formed on the distal and proximal sides, respectively.

The occluder 70 can be secured in the petal configuration by a catch system that holds the ends of the tube together, in a reduced axial length configuration, certain embodiments of which are described below. The term "catch system" describes the portion/aspect of the device that secures the device in the deployed configuration; it may be a single piece or a group of connected or assembled pieces. According to one embodiment of the invention, a catch system for an occluder includes a catch member and a locking cap. The catch member is a portion of the catch system that is slidably disposed within the occluder and engages with the occluder to define the axial length in the deployed configuration and is described in more detail below. The locking cap secures the catch member to the occluder in the deployed configuration. In general, references to "occluder 70" herein may be inclusive of the catch system, depending on the context, for example, unless separately listed or otherwise stated.

This particular type of occluder 70 and its delivery sequences are described for purposes of illustration and explanation; of course, other types of occluders can be deployed using the deployment catch systems described herein. The catch member 50, as illustrated and referenced in FIG. 8, is disposed in a radially central location in the occluder 70 and is schematically illustrated as a separate piece than the occluder 70. According to some embodiments, the catch member 50 may be fixed to and holds one end of the tube that forms occluder 70, preferably the distal end of the tube 76. As illustrated, a distal flange 152 of the catch member 50 may engage the distal end 76 of the tube.

The other end of the tube forming occluder 70, preferably the proximal end of the tube, is able to move with respect to the catch member 50 (and especially the catch system) so that the axial length of the tube can be shortened, thereby forming distal and proximal petals 72 and 82. The inside surface of the tube is able to slide over the catch member 50 as the occluder 70 moves from the delivery configuration to the deployed configuration, so that, when the proximal end 86 of the tube rests against a proximal catch surface of the catch member, the occluder 70 is secured in its deployed configuration.

One embodiment of a catch system of the present invention will now be described with reference to FIGS. 9-15. FIG. 9 is an exploded perspective view of the components of a catch system 45 that includes catch member 50 that is disposed in an axial passage of the occluder 70. The axial passage may be disposed in a radially central portion of the occluder 70 in some embodiments. The catch system 45 also includes a locking funnel cap 64. The catch member 50 connects to a delivery wire 52 and the locking funnel cap 64 connects to a delivery catheter 60 of the delivery system. As described hereinbelow, in this embodiment, the catch member 50 and funnel locking cap 64 provide a mechanism for holding the occluder 70 in the deployed configuration. The catch member 50 includes distal flange 152 on its distal side as illustrated in FIGS. 6-8. The distal flange 152 causes the catch member 50 to engage and hold the distal end of the occluder 70. In some embodiments, the distal flange 152 of the catch member 50 is fixed to the occluder. 70. In other embodiments, the distal flange 152 of the catch member 50 is not fixed to the occluder 70, allowing the catch member 50 to rotate with respect to the occluder 70.

According to one embodiment, the catch member 50 includes a proximal flange 92 at its proximal side. As illustrated in FIG. 9, the proximal flange 92 of the catch member 50 includes a catch surface 92a. Typically, the catch member 50 has an axial length of about 5-30 mm and a diameter of approximately 0.5-3 mm. The axial length of the catch member 50 approximately corresponds to the axial length of the occluder 70 in the deployed configuration. A delivery system for the device includes in part the delivery catheter 60 in which the occluder 70 and the catch system 45 are provided and the delivery wire 52 for holding and deploying the catch system 45. The proximal end of the catch member 50 includes internal threads 56 and during delivery is threadably connected to the distal end of the delivery wire 52.

With continuous reference to FIG. 9, the locking funnel cap 64 is a separate component from the occluder 70 and the catch member 50. In one embodiment, the locking funnel cap 64 includes a substantially cylindrical body, with a hollow core including internal threads 166, and, preferably, a smooth exterior. The distal portion of internal threads 166 of locking funnel cap 64 is adapted to be threaded on external threads 192 of the proximal end 86 of the occluder 70. The distal portion of internal threads 166 that are adapted to threadably connect to the proximal end of the occluder 70 have a tapered inner diameter in one segment, characterized by a funnel-shape. The distal portion of internal threads 166 have a first diameter at the distal end and a second, smaller diameter proximal from the distal end. The proximal portion of the internal threads 166 of the locking funnel cap 64 is adapted to be connected with the delivery catheter 60. The body of the locking funnel cap 64 may be tapered to follow the shape of the internal threads 166 in certain embodiments.

With continuous reference to FIG. 9, the proximal end 86 of the occluder 70 may include notches or slits 186. Notches 186 allow the proximal end 86 of the occluder 70 to move radially inward, so that the proximal end 86 of the occluder 70 is compressed, when the distal portion of the locking funnel cap 64 is fully threaded on the proximal end 86 of the occluder 70. According to one embodiment, the funnel-shaped internal thread 166 of the locking funnel cap 64 forces the proximal ends of the occluder 70 in a radially inward position to reduce the overall dimension of the inside passage of the tube at the proximal end of the occluder 70. According to one embodiment, during delivery, as the axial length of the occluder 70 is reduced, the proximal end 86 of the occluder 70 slides over the catch member 50. The locking funnel cap 64 is then fully engaged with the proximal end 86 of the occluder 70 compressing the proximal end 86 of the occluder 70 inward, resulting in a smaller diameter for the inside surface of the proximal end 86 of the occluder 70. The catch surface 92a of the catch member 50 has a sufficient dimension, e.g., greater than the diameter of the inside surface of the compressed proximal end 86 of the occluder 70, such that the occluder 70 can no longer expand axially, and thus the occluder 70 is maintained in its deployed configuration.

FIG. 10 illustrates the locking funnel cap 64 screwed into place with the end face 190 of the proximal end 86 of the occluder 70 is disposed in a radially inward manner. In this configuration, the surface 92a of the catch member 50 contacts the end face 190 of the proximal end 86 of the occluder 70, and the proximal flange 92 of the catch member 50 prevents the proximal end 86 of the occluder 70 from moving proximally, thereby holding the occluder 70 in a deployed configuration. The proximal flange 92 and/or catching surface 92a of the catch member 50 in a preferred embodiment is dimensioned such that the an outer dimension of the proximal flange exceeds the inner diameter of the radially centric axial passage of the radially compressed proximal end 86 of the occluder 70, in order to effectively hold the proximal end of the occluder 70 in its deployed configuration, but does not significantly exceed the outer diameter of the radially compressed proximal end 86 of the occluder 70, if at all. This dimension is preferably matched to an inner dimension of the locking funnel cap 64. Other configurations of the catch assembly are possible and within the scope of the present invention. In certain embodiments, the funnel segment of internal threads 166 could be disposed closer to the distal end of the locking funnel cap 64 or further from the distal end of the locking funnel cap 64. The wider end of the funnel segment, i.e., the portion having a larger inner diameter will be distal relative to the narrower end of the funnel segment, i.e., the portion having a smaller inner diameter.

Catch member 50 and/or the locking funnel cap 64 could be made of the same or different material than the occluder 70. According to one embodiment, catch system 45, including catch member 50 and/or the locking funnel cap 64, as illustrated in FIGS. 9-15, are made of any metal or polymer. In another embodiment, catch system 45 is made of biocompatible metal or polymer. In an alternative embodiment, catch system 45 is made of bioabsorbable or shape memory material.

In an alternative embodiment, catch system 45 is made of a bioabsorbable material. Exemplary bioabsorbable materials include polymers, such as polyhydroxyalkanoate compositions, for example poly-4-hydroxybutyrate (P4HB) compositions, disclosed in U.S. Pat. No. 6,610,764, entitled Polyhydroxyalkanoate Compositions Having Controlled Degradation Rate and U.S. Pat. No. 6,548,569, entitled Medical Devices and Applications of Polyhydroxyalkanoate Polymers, both of which are incorporated by reference in their entirety.

With continuous reference to FIG. 9, the catch member 50 is threadably connected to a delivery wire 52. In a preferred embodiment, the delivery wire 52 includes external threads 54, which can be threaded into internal threads 56 disposed in a radially centric position at the proximal end of the catch member 50. In an alternative embodiment, internal threads 56 are disposed in a radially central position at center, distal, or any location of the catch member 50. In an alternative embodiment, the threaded connection between the catch member 40 and the delivery wire 52 is reversed having male threads at the proximal end of the catch member 50 and female threads at the distal end of the delivery wire 52.

With continuous reference to FIG. 9, the locking funnel cap 64 is threadably connected to a delivery catheter 60. In a preferred embodiment, the delivery catheter 60 includes external threads 182, which can be threaded into proximal portion of the internal threads 166 of the locking funnel cap 64. In another embodiment, the threaded connection between the proximal end of the locking funnel cap 64 and the distal end 62 of the delivery catheter 60 is reversed, having male threads at the proximal end of the locking funnel cap 64 and female threads at the distal end 62 of the delivery catheter 60.

According to another embodiment, the connection between the delivery catheter 60 and the locking funnel cap 64 and/or the connection between delivery wire 52 and the catch member 50 can be any other suitable mechanism as described in, for example, U.S. patent application Ser. No. 11/235,661, incorporated by reference herein in its entirety.

FIG. 11 illustrates a perspective view of the catch assembly which locks the occluder 70 in its deployed configuration, with the locking funnel cap 64 shown in phantom lines. Notches 186 are illustrated as open in FIG. 9 and as closed in FIG. 11. According to one embodiment, notches 186 are closed, i.e., no gap exists when the locking funnel cap 64 is fully engaged with the proximal end 86 of the occluder 70. According to an alternative embodiment, notches 186 are partially closed, i.e., a small gap still exists when the locking funnel cap 64 is fully engaged with the proximal end 86 of the occluder 70.

Figure 12:
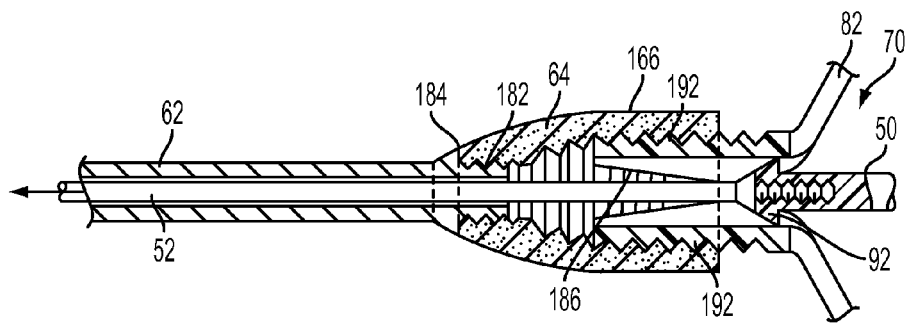
FIGS. 12-15 are cross-sectional detail views of the deployment process of an occluder according to an embodiment of the present invention.

FIGS. 12-15 illustrate an exemplary locking sequence with the above illustrated catch system 45 during the deployment process of the occluder 70. As illustrated in FIG. 12, upon exposing both the distal and the proximal portions of the occluder 70 at the treatment site, the delivery wire 52, connected to the catch member 50, extends proximally through the radially central passageway of the proximal end 86 of the occluder 70. The distal and proximal petals 72 and 82 (not shown), form as the proximal portion of the catch member 50 passes through the radially central passageway of proximal end 86 of the occluder 70. This can be accomplished by pulling the delivery wire 52 in the direction of the arrow, illustrated in FIG. 12.

Figure 13:
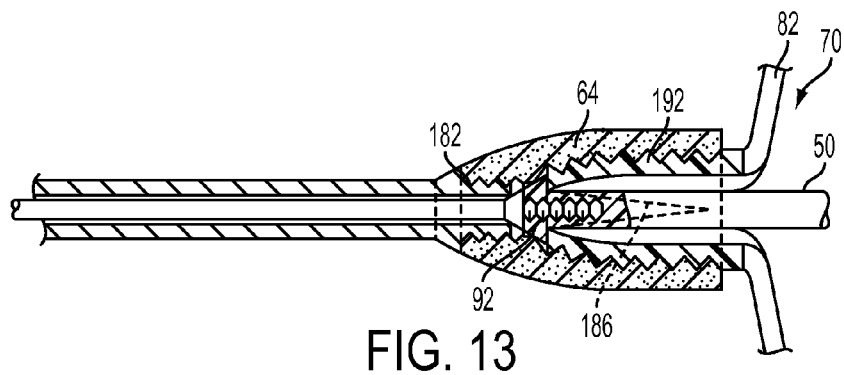

As illustrated in FIG. 13, as the proximal end of the catch member 50 extends beyond the end face 190 of the proximal end 86 of the occluder 70, the locking funnel cap 64 is advanced distally, by rotational motion, relative to the proximal end 86 of the occluder 70. As the locking funnel cap 64 advances distally, the-proximal end 86 of the occluder 70 moves radially inward, following the inner threaded profile of the locking funnel cap 64, so that the surface 92a of the catch member 50 contacts the end face 190 of the proximal end 86 of the occluder 70 and the proximal flange 92 of the catch member 50 prevents the proximal end 86 of the occluder 70 from moving proximally, thereby holding the occluder 70 in a deployed configuration.

Figure 14:
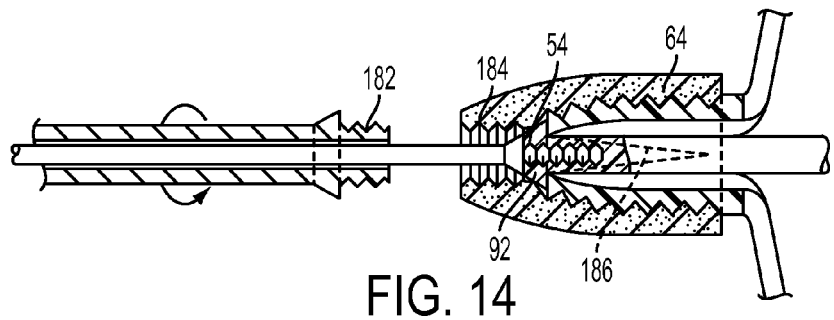
Figure 15:
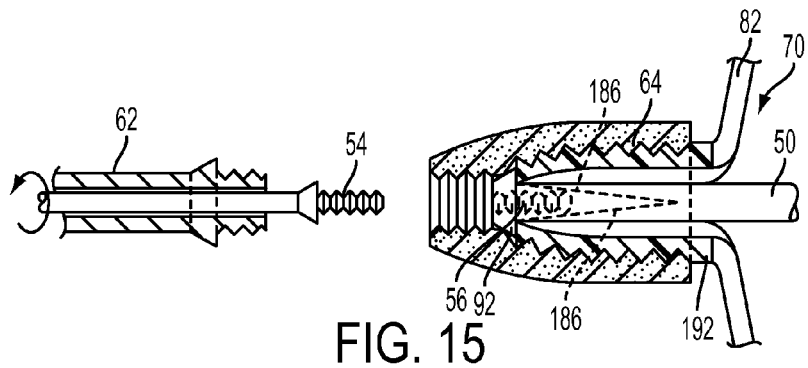

As illustrated in FIG. 14, once the locking funnel cap 64 is fully engaged with the proximal end 86 of the occluder 70, thereby locking the occluder 70 in its deployed configuration, the delivery catheter 60 can be removed by disengaging the connection between the locking funnel cap 64 and the delivery catheter 60, and then retracting the delivery catheter 60 proximally. With the delivery wire 52 still connected to the catch member 50, the deployment of the occluder 70 can now be assessed. If deployment of the occluder 70 is not satisfactory, the occluder 70 can be retrieved by reversing the locking step as described above. Upon satisfaction with the deployment of the occluder 70, the delivery wire 52 can be removed as illustrated in FIG. 15. After the delivery wire 52 is removed, the catch system 45, including the locking funnel cap 64 and catch member 50 remains in place to secure the occluder 70 in the deployed configuration. If retrieval or redeployment is desired, the deployment steps can readily be reversed to collapse the occluder 760 to its delivery configuration. In particular, the locking funnel cap 64 can be unscrewed to cause the proximal end of the occluder 70 to be released. The catch member 50 can be drawn back into the occluder 70.

It will be understood that in the illustrated embodiment the design of the catch system 45 is such that the torque required to unscrew the distal portion of the locking funnel cap 64 from the proximal end 86 of the occluder 70 is larger than the torque required to unscrew the distal end 62 of the delivery catheter 60 from the proximal portion of the locking funnel cap 64. This can be achieved by selecting appropriate combinations of materials, sizes, pitches, and/or other properties of the threaded connections described herein.

In an alternate embodiment, the proximal end 86 of the occluder 70 is sufficiently pliable so that notches 186 are unnecessary. In such a configuration, the material of the proximal end 86 of the occluder 70 is deformed when engaged with the locking funnel cap 64, so that the catch member 50 is prevented from passing through the central passageway of the proximal end 86 of the occluder 70, thereby locking the occluder 70 in its deployed configuration.

The embodiments and techniques described here are described preferably for use with a device made of a polymer and formed from a single tube, or tube-like structure. While the device is thus shown as being substantially formed from a single tubular body, the catch mechanism as described in the embodiments above could be used with other types of devices, including those formed from many pieces, and including devices formed from other materials, including metals, polymers, stainless steel or nitinol.

The term "bioabsorbable," as used in the description above, is also understood to mean "bioresorbable."

In cases in which the device is made of a polymer, it can be desirable to add an additive or coating to the material to make it radiopaque to make it more visible in a wider variety of imaging techniques.

It will be appreciated that while a particular sequence of steps has been shown and described for purposes of explanation, the sequence may be varied in certain respects, or the steps may be combined, while still obtaining the desired deployment or in some cases to effect deployment in a particular way. For example, the delivery catheter may be advanced or retracted at varying times and in varying degrees, the proximal and distal portions of the occluder may be deployed into the petal configuration in a different sequence, etc. In addition, the steps could be automated.

What is claimed is:

1. A collapsible medical device for occluding an aperture in a body, the medical device having a first configuration with a reduced profile and a second configuration with an expanded profile, the medical device having a proximal side and a distal side, the medical device being adapted to be delivered through a delivery system into a desired delivery location, the medical device comprising:
   an occluder portion movable from a reduced profile configuration to an expanded profile configuration, the occluder portion having a proximal end and a distal end, the occluder portion including an axial passage along the length of the occluder portion; and
   a catch member for holding the occluder portion in the expanded profile configuration, the catch member adapted to be disposed in the axial passage of the occluder portion, the catch member having a proximal end, a distal end, and an axial length between the proximal and distal ends, the distal end of the catch member being adapted to engage the distal end of the occluder portion, the proximal end of the catch member being adapted to engage the proximal end of the occluder portion in the expanded profile configuration; and
   a separate locking cap adapted to engage the proximal end of the occluder portion in the expanded profile configuration,
   wherein the locking cap has a proximal portion and a distal portion, and the distal portion of the locking cap includes first internal threads for threadably connecting to the proximal end of the occluder and the proximal end of the occluder includes external threads, and wherein a proximal portion of the locking cap includes second internal threads for threadably connecting to a delivery system.

2. The medical device of claim 1, wherein the catch member includes a proximal flange that engages the proximal end of the occluder portion.

3. The medical device of claim 1, wherein first internal threads have a first diameter adjacent to the distal end of the locking cap and a second diameter less than the first diameter away from the distal end of the locking cap.

4. The medical device of claim 3, wherein at least a portion of an interior cavity of the locking cap defined by first internal threads has a funnel shape.

5. The medical device of claim 1, wherein the proximal end of the occluder portion is compressible in a radially inward direction and is compressed when the locking cap is secured.

6. The medical device of claim 5, wherein the proximal end of the occluder portion includes an axial notch.

7. The medical device of claim 6, wherein the axial notch remains partially open when the locking cap is secured.

8. The medical device of claim 1, wherein the catch member and locking cap are made of a bioabsorbable material.

9. The medical device of claim 1, wherein the catch member and locking cap are made of a bioabsorbable polymer.

10. A collapsible medical device for occluding an aperture in a body, the medical device having a first configuration with a reduced profile and a second configuration with an expanded profile, the medical device having a proximal side and a distal side, the medical device being adapted to be delivered through a delivery system into a desired delivery location, the medical device comprising:
    an occluder portion movable from a reduced profile configuration to an expanded profile configuration, the occluder portion having a reduced axial length in the expanded profile configuration, the occluder portion having a proximal end and a distal end, the occluder portion including an axial passage along the length of the occluder portion;
    a catch member for holding the occluder portion in the expanded profile configuration, the catch member being adapted to be disposed in the axial passage of the occluder portion, the catch member having a proximal end, a distal end, and an axial length between the proximal and distal ends, the distal end of the catch member including a distal flange for holding the distal end of the occluder portion, the proximal end of the catch member including a catching surface for engaging the proximal end of the occluder portion in the expanded profile configuration, wherein the catch member includes a proximal flange that engages the proximal end of the occluder portion; and
    a separate locking cap that engages the proximal end of the occluder portion in the expanded profile configuration and prevents the proximal flange from being drawn into the axial passage, wherein the locking cap has a proximal portion and a distal portion, and the distal portion of the locking cap includes first internal threads for threadably connecting to the proximal end of the occluder and the proximal end of the occluder includes external threads, and wherein a proximal portion of the locking cap includes second internal threads for threadably connecting to a delivery system.

11. The medical device of claim 10, wherein first internal threads have a first diameter adjacent to the distal end of the locking cap and a second diameter less than the first diameter away from the distal end of the locking cap.

12. The medical device of claim 11, wherein at least a portion of an interior cavity defined by first internal threads has a funnel shape.

13. The medical device of claim 10, wherein the proximal end of the occluder portion is compressible in a radially inward direction and is compressed when the locking cap is secured.

14. The medical device of claim 13, wherein the proximal end of the occluder portion includes an axial notch.

15. The medical device of claim 14, wherein the axial notch remains partially open when the locking cap is secured.

16. The medical device of claim 10, wherein the catch member and locking cap are made of a bioabsorbable material.

17. The medical device of claim 16, wherein the catch member and locking cap are made of a bioabsorbable polymer.

\* \* \* \* \*